United States Patent [19]

DeLuca et al.

[11] Patent Number: 5,565,589
[45] Date of Patent: Oct. 15, 1996

[54] 17-FORMYL-5,6-TRANS-VITAMIN D COMPOUNDS

[75] Inventors: Hector F. DeLuca, Deerfield, Wis.; Rafal R. Sicinski, Warsaw, Poland

[73] Assignee: Wisconsin Alumni Research Foundation, Madison, Wis.

[21] Appl. No.: 147,663

[22] Filed: Nov. 3, 1993

[51] Int. Cl.$^6$ .................................................. C07C 401/00
[52] U.S. Cl. ............................................................ 552/653
[58] Field of Search ........................... 552/653; 556/436, 556/449, 482; 568/445

[56] References Cited

U.S. PATENT DOCUMENTS

| 4,338,250 | 7/1982 | DeLuca et al. |  |
|---|---|---|---|
| 4,758,383 | 7/1988 | Tachibana . |  |
| 4,769,181 | 9/1988 | DeLuca et al. |  |
| 4,857,518 | 8/1989 | DeLuca et al. |  |
| 4,866,048 | 9/1989 | Calverley et al. |  |
| 4,973,584 | 11/1990 | DeLuca et al. |  |
| 5,089,641 | 2/1992 | DeLuca et al. | 552/653 |
| 5,116,573 | 5/1992 | Yamada et al. | 552/653 |
| 5,182,393 | 1/1993 | Yianikouros | 552/653 |
| 5,206,230 | 4/1993 | Ikekawa et al. | 514/167 |
| 5,250,523 | 10/1993 | DeLuca et al. |  |
| 5,260,290 | 11/1993 | DeLuca et al. |  |

FOREIGN PATENT DOCUMENTS

| 184112 | 6/1986 | European Pat. Off. . |
| 8909573 | 11/1989 | United Kingdom . |
| WO89/10351 | 11/1989 | WIPO . |
| WO89/10352 | 11/1989 | WIPO . |

OTHER PUBLICATIONS

Biochemistry, vol. 29, No. 1, 1990, pp. 190–196, "24–Homologated 1,25–Dihydroxyvitamin D Compounds: Separation of Calcium and Cell Differentiation Activities", Kato Perlman et al.

Matoba et al, "Structural Modification of Bioactive Compounds. 1. Syntheses of Vitamin D Analogues 1.", Chemical and Pharmaceutical Bulletin, vol. 32, No. 4, Apr. 1984, Tokyo, Japan, pp. 1416–1422.

Murayama et al, "Synthesis and Immunoregulating Activity of Vitamin D Analogues Bearing Pregnane Side Chains", Bioorganic & Medicinal Chemistry Letters, vol. 2, No. 10, 1992, Great Britain, pp. 1289–1292.

Perlman et al, "20–Oxopregnacalciferols: Vitamin D Compounds that Bind the Progesterone Receptor", Tetrahedron Letters, vol. 35, No. 15, Apr. 1994, Great Britain, pp. 2295–2298.

Murayama, et al *Bioorganic & Medicinal Chemistry Letters* vol. 2(10), pp. 1289–1292 (1992).

Murari, et al. *Journal of Steroid Biochemistry*, vol. 17, pp. 615–619 (1982).

*Primary Examiner*—Kimberly J. Prior
*Attorney, Agent, or Firm*—Andrus, Sceales, Starke & Sawall

[57] ABSTRACT

The invention is drawn to 17-formyl vitamin D compounds having the following formula

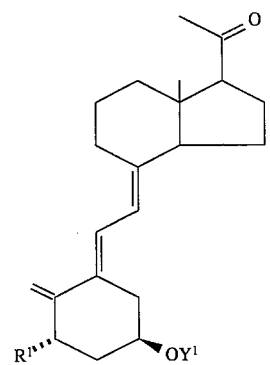

The compounds are intermediates in the production of 5,6-trans-(E)-20(22)-Dehydrovitamin D compounds which are useful for the treatment of diseases where bone formation is desired, such as osteoporosis, and for the treatment of diseases characterized by abnormal cell differentiation or cell proliferation, such as psoriasis.

1 Claim, No Drawings

5,565,589

17-FORMYL-5,6-TRANS-VITAMIN D COMPOUNDS

This invention was made with United States Government support awarded by the National Institutes of Health (NIH), Grant No. DK-14881. The United States Government has certain rights in this invention.

BACKGROUND OF THE INVENTION

This invention relates to biologically active vitamin D compounds. More specifically, the invention relates to (E)-20(22)-dehydrovitamin D compounds, to a general process for their preparation, and to their use in treating osteoporosis and psoriasis.

With the discovery of $1\alpha,25$-dihydroxyvitamin $D_3$ as the active form of the vitamin has come an intense investigation of analogs of this hormonal form of vitamin D with the intent of finding analogs that have selective activity. By now, several compounds have been discovered which carry out the differentiative role of 1,25-dihydroxyvitamin $D_3$ while having little or no calcium activity. Additionally, other compounds have been found that have minimal activities in the mobilization of calcium from bone while having significant activities in stimulating intestinal calcium transport. Modification of the vitamin D side chain by lengthening it at the 24-carbon has resulted in loss of calcium activity and either an enhancement or undisturbed differentiative activity. Placing the 24-methyl of $1\alpha,25$-dihydroxyvitamin $D_2$ in the epi-configuration appears to diminish activity in the mobilization of calcium from bone. On the other hand, increased hydrophobicity on the 26- and 27-carbons seems to increase the total activity of the vitamin D compounds provided the 25-hydroxyl is present.

Several of these known compounds exhibit highly potent activity in vivo or in vitro, and possess advantageous activity profiles. Thus, some of these compounds are in use, or have been proposed for use, in the treatment of a variety of diseases such as renal osteodystrophy, vitamin D-resistant rickets, osteoporosis, psoriasis, and certain malignancies.

It is well known that females at the time of menopause suffer a marked loss of bone mass giving rise ultimately to osteopenia, which in turn gives rise to spontaneous crush fractures of the vertebrae and fractures of the long bones. This disease is generally known as postmenopausal osteoporosis and presents a major medical problem, both in the United States and most other countries where the lifespan of females reaches ages of at least 60 and 70 years. Generally, the disease which is often accompanied by bone pain and decreased physical activity, is diagnosed by one or two vertebral crush fractures with evidence of diminished bone mass. It is known that this disease is accompanied by diminished ability to absorb calcium, decreased levels of sex hormones, especially estrogen and androgen, and a negative calcium balance.

Similar symptoms of bone loss characterize senile osteoporosis and steroid-induced osteoporosis, the latter being a recognized result of long term glucocorticoid (cortico-steroid) therapy for certain disease states.

Methods for treating the disease have varied considerably but to date no totally satisfactory treatment is yet known. A conventional treatment is to administer a calcium supplement to the patient. However, calcium supplementation by itself has not been successful in preventing or curing the disease. Another conventional treatment is the injection of sex hormones, especially estrogen, which has been reported to be effective in preventing the rapid loss of bone mass experienced in postmenopausal women. This technique, however, has been complicated by the fact of its possible carcinogenicity. Other treatments for which variable results have been reported, have included a combination of vitamin D in large doses, calcium and fluoride. The primary problem with this approach is that fluoride induces structurally unsound bone, called woven bone, and in addition, produces a number of side effects such as increased incidence of fractures and gastrointestinal reaction to the large amounts of fluoride administered. Another suggested method is to block bone resorption by injecting calcitonin or providing phosphonates.

U.S. Pat. No. 4,225,596 suggests the use of various metabolites of vitamin $D_3$ for increasing calcium absorption and retention within the body of mammals displaying evidence of or having a physiological tendency toward loss of bone mass. The metabolites specifically named in that patent, i.e., $1\alpha$-hydroxyvitamin $D_3$, $1\alpha,25$-hydroxyvitamin $D_2$ $1\alpha,25$-dihydroxyvitamin $D_3$, $1\alpha,25$-dihydroxvitamin $D_2$ and $1\alpha,24,25$-trihydroxyvitamin $D_3$, although capable of the activity described and claimed in that patent are also characterized by the disadvantage of causing hypercalcemia especially if used with the conventional calcium supplement treatment. Therefore, use of these compounds to treat osteoporosis has not been widely accepted. U.S. Pat. Nos. 3,833,622 and 3,901,928 respectively suggest using the hydrate of 25-hydroxyvitamin $D_3$ and $1\alpha$-hydroxyvitamin $D_3$ for treatment of osteoporosis in a general expression of utility for those compounds. It is well known both of those compounds express traditional vitamin D-like activity, including the danger of hypercalcemia.

U.S. Pat. No. 4,588,716 also suggests the use of $1\alpha,25$-dihydroxy-24-epi-vitamin $D_2$ to treat bone disorders characterized by the loss of bone mass, such as osteoporosis. This compound expresses some of the vitamin D-like characteristics affecting calcium metabolism such as increasing intestinal calcium transport and stimulating the mineralization of new bone. It also has the advantage of minimal effectiveness in mobilizing calcium from bone. The 24-epi compound may be administered alone or in combination with a bone mobilization inducing compound such as a hormone or vitamin D compound such as $1\alpha$-hydroxyvitamin $D_3$ or $D_2$ or $1\alpha,25$-hydroxyvitamin $D_3$ or $D_2$.

U.S. Pat. No. 5,194,431 discloses the use of 24-cyclopropane vitamin $D_2$ compounds in treating osteoporosis. Also, U.S. Pat. No. 4,851,401 discloses the use of cyclopentano 1,25-dihydroxyvitamin $D_3$ compounds in the treatment of osteoporosis and related diseases.

In an ongoing effort to develop a treatment for osteoporosis, and to investigate the biological activity of vitamin D compounds, the carbon 20 position of the side-chain was investigated to determine its potential. Altering the order of substituents or the substitution pattern on carbon 20 could result in a change of minimum energy position for conformations around the $C_{17}$–$C_{20}$ bond, and consequently, in a change of side-chain orientation with respect to the ring system. Orientation of the side-chain with respect to the ring system and configuration on the $C_{20}$ may have important consequences for biological properties of cholestane derivatives, in particular vitamin D compounds. It is well documented that binding of $1\alpha,25$-dihydroxyvitamin $D_3$ involves active centers in the ring A and triene system as well as in the side-chain. Altering the "normal configuration" around $C_{17}$–$C_{20}$ bond in vitamin D could change the distance between active centers within the molecule, and thus result in a change in activity of such compounds.

SUMMARY OF THE INVENTION

The present invention provides novel (E)-20(22)-dehydrovitamin D compounds exhibiting a desired, and highly advantageous, pattern of biological activity. These compounds are characterized by a marked intestinal calcium transport activity, as compared to that of 1α,25-dihydroxyvitamin $D_3$, while exhibiting much lower activity than 1α,25-dihydroxyvitamin $D_3$ in their ability to mobilize calcium from bone. Hence, these compounds are highly specific in their calcemic activity. Their preferential activity on intestinal calcium transport and reduced calcium mobilizing activity in bone allows the in vivo administration of these compounds for the treatment of metabolic bone diseases where bone loss is a major concern. Because of their preferential calcemic activity, these compounds would be preferred therapeutic agents for the treatment of diseases where bone formation is desired, such as osteoporosis, osteomalacia and renal osteodystrophy. These compounds also have relatively high HL-60 cell differentiation activity which makes them particularly suitable for use in treating diseases characterized by abnormal cell differentiation and/or cell proliferation, such as psoriasis.

Structurally, the key feature of the compounds having these desirable biological attributes is that they are analogs of vitamin $D_3$ in which a double bond has been introduced into the side-chain between carbons 20 and 22. Thus, the compounds of this type are characterized by structures I and II:

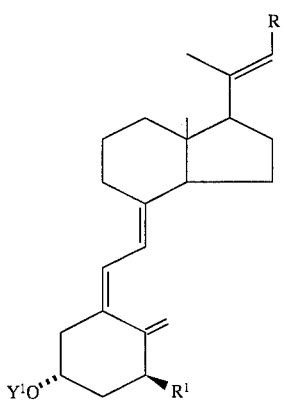

I

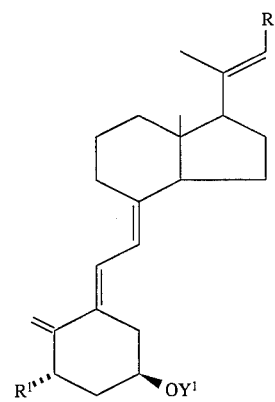

II where $Y^1$ may be hydrogen or a hydroxy-protecting group, $R^1$ represents hydrogen, hydroxy or protected hydroxy, and where R is hydrogen, aryl, alkyl, hydroxyalkyl or fluoroalkyl group, or R may represent the following side chain fragment:

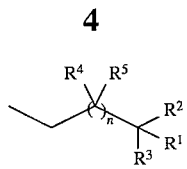

wherein $R^1$ is as defined above, $R^2$ and $R^3$ are each selected from the group consisting of alkyl, hydroxyalkyl and fluoroalkyl, or, when taken together represent the group —$(CH_2)m$— where m is an integer having a value of from 2 to 5, $R^4$ is selected from the group consisting of hydrogen, hydroxy, fluorine, O-acyl, alkyl, hydroxyalkyl and fluoroalkyl, $R^5$ is selected from the group consisting of hydrogen, fluorine, alkyl, hydroxyalkyl and fluoroalkyl, and wherein n is an integer having a value of from 1 to 5.

The present invention, therefore, provides novel compounds showing preferential activity on intestinal calcium transport and reduced calcium mobilizing activity in bone, and are useful for the treatment of metabolic bone diseases, such as osteoporosis, where bone loss is a major concern. High cell differentiation activity also makes them suitable for treating diseases characterized by abnormal cell differentiation and/or cell proliferation, such as psoriasis. More specifically, the preferred compound is (E)-20(22)-dehydro-1α,25 dihydroxyvitamin $D_3$.

This invention also provides novel intermediate compounds formed during the synthesis of the end products. Structurally, the intermediate compounds are characterized by the following general structure:

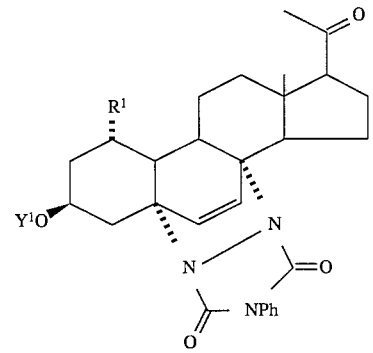

where $Y^1$ and $R^1$ are as previously defined herein.

Other key intermediates are characterized by the following general structures:

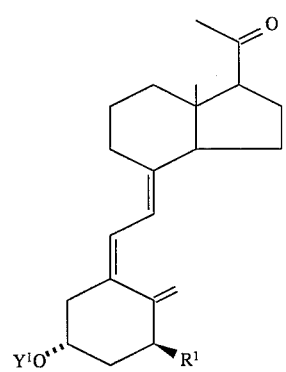

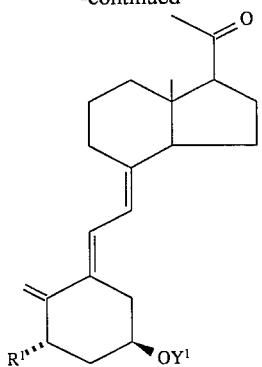

where $Y^1$ and $R^1$ are as previously defined herein.

In another aspect of the invention, it has now been found that the loss of bone mass, which is characteristic of osteoporosis may be effectively treated by the administration of a (E)-20(22)-dehydrovitamin D compound in sufficient amounts to increase bone mass. More specifically, a method of treating osteoporosis comprises the administration of an effective amount of a (E)-20(22)-dehydrovitamin D compound, preferably (E)-20(22)-dehydro-1α,25-dihydroxyvitamin $D_3$. The above compounds may be administered alone or in combination with other pharmaceutically acceptable agents. Dosages of from not less than about 0.5 μg/day to not more than about 50 μg/day of the individual compound per se, or in combinations, are generally effective. This method has the distinct advantage that it will restore bone mass due to the preferential intestinal activity and the insignificant bone mobilization activity of these compounds. Further, these compounds advantageously will not cause hypercalcemia even if the compound is administered continuously on a daily basis, as long as the appropriate compound dosages are used, it being understood that the dosage levels will be adjusted dependent on the response of the subject as monitored by methods known to those skilled in the art.

The above method, involving the administration of the indicated dosages of (E)-20(22)-dehydrovitamin D compounds such as (E)-20(22)-dehydro-1α,25-dihydroxyvitamin $D_3$ is effective in restoring or maintaining bone mass, and thus provides a novel method for the treatment or prevention of various forms of osteoporosis such as postmenopausal osteoporosis, senile osteoporosis and steroid-induced osteoporosis. It will be evident that the method will find ready application for the prevention or treatment of disease states other than those named, in which the loss of bone mass is an indication.

In still another aspect of the invention, it has now been found that abnormal cell differentiation and/or cell proliferation, which is characteristic of diseases such as psoriasis, may be effectively treated by the administration of a (E)-20(22)-dehydrovitamin D compound in sufficient amounts to treat the disease. More specifically, a method of treating psoriasis comprises the administration of an effective amount of a (E)-20(22)-dehydrovitamin D compound, preferably (E)-20(22)-dehydro-1α,25-dihydroxyvitamin D3. The above compounds may be administered alone or in combination with other pharmaceutically acceptable agents. Dosages of from not less than about 0.5 μg/day to not more than about 50 μg/day of the individual compound per se, or in combinations, are generally effective. This method has the distinct advantage that it will treat the disease and further these compounds advantageously will not cause hypercalcemia even if the compound is administered continuously on a daily basis, as long as the appropriate compound dosages are used, it being understood that the dosage levels will be adjusted dependent on the response of the subject as monitored by methods known to those skilled in the art.

DETAILED DESCRIPTION OF THE INVENTION

In this specification and the claims, the term "hydroxy-protecting group" refers to any group commonly used for the protection of hydroxy functions during subsequent reactions, including, for example, acyl or alklsilyl groups such as trimethylsilyl, triethylsilyl, t-butyldimethylsilyl and analogous alkylated silyl radicals, or alkoxyalkyl groups such as methoxymethyl, ethoxymethyl, methoxyethoxymethyl, tetrahydrofuranyl or tetrahydropyranyl. A "protected-hydroxy" is a hydroxy function derivatized by one of the above-hydroxy-protecting groupings. "Alkyl" signifies a straight-chain or branched hydrocarbon radical of 1 to 10 carbons in all its isomeric forms, such as methyl, ethyl, propyl, isopropyl, butyl, isobutyl, pentyl, etc., and the terms "hydroxyalkyl" and "flouoroalkyl" refer to such an alkyl radical substituted by one or more hydroxy or fluoro groups respectively. The term "acyl" means an alkanoyl group of 1 to 6 carbons in all its isomeric forms, such as formyl, acetyl, propionyl, etc. or an aroyl group, such as benzoyl, nitrobenzoyl or halobenzoyl, or a dicarboxylic acyl group such as oxalyl, malonyl, succinoyl, glutaroyl, or adipoyl. The term "aryr" signifies a phenyl-, or an alkyl-, nitro- or halo-substituted phenyl group. A wavy line to the substituents at C-20 and C-22 indicate that these substituents may have either the R or S configuration.

The vitamin D compounds useful in the present treatment are (E)-20(22)-dehydrovitamin D compounds, preferably (E)-20(22)-dehydro-1α,25-dihydroxyvitamin $D_3$. The above compounds may be administered alone or in combination with other pharmaceutically acceptable agents.

The (E)-20(22)-dehydrovitamin D compounds or combinations thereof can be readily administered as sterile parenteral solutions by injection or intravenously, or by alimentary canal in the form of oral dosages, or transdermally, or by suppository or by topical formulations. Doses of from about 0.5 micrograms to about 50 micrograms per day of the compounds per se, or in combination with other 1α-hydroxylated vitamin D compounds, the proportions of each of the compounds in the combination being dependent upon the particular disease state being addressed and the degree of bone mineralization and/or bone mobilization desired, are generally effective to practice the present invention. In all cases sufficient mounts of the compound should be used to restore bone mass. Amounts in excess of about 50 micrograms per day or the combination of that compound with other 1α-hydroxylated vitamin D compounds, are generally unnecessary to achieve the desired results, may result in hypercalcemia, and may not be an economically sound practice. In practice the higher doses are used where therapeutic treatment of a disease state is the desired end while the lower doses are generally used for prophylactic purposes, it being understood that the specific dosage administered in any given ease will be adjusted in accordance with the specific compounds being administered, the disease to be treated, the condition of the subject and the other relevant medical facts that may modify the activity of the drug or the response of the subject, as is well known by those skilled in the art. For example, to be effective, the (E)-20(22)-dehydro-1α,25-dihydroxyvitamin $D_3$ compound is preferably administered in a dosage range of 0.5–50

μg/day. In general, either a single daily dose or divided daily dosages may be employed, as is well known in the art.

Dosage forms of the various compounds can be prepared by combining them with non-toxic pharmaceutically acceptable carriers to make either immediate release or slow release formulations, as is well known in the art. Such carriers may be either solid or liquid such as, for example, corn starch, lactose, sucrose, peanut oil, olive oil, sesame oil and propylene glycol. If a solid carrier is used the dosage form of the compounds may be tablets, capsules, powders, troches or lozenges. If a liquid carrier is used, soft gelatin capsules, or syrup or liquid suspensions, emulsions or solutions may be the dosage form. The dosage forms may also contain adjuvants, such as preserving, stabilizing, wetting or emulsifying agents, solution promoters, etc. They may also contain other therapeutically valuable substances.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

The topical compositions of this invention are formulated preferably as creams, lotions, ointments and the like by choice of appropriate carriers. Suitable carriers include vegetable or mineral oils, white petrolatum (white soft parafin), branched chain fats or oils, animal fats and high molecular weight alcohol (greater than $C_{12}$). The preferred carriers are those in which the active ingredient is soluble. Emulsifiers, stabilizers and antioxidants may also be included as well as agents imparting color or fragrance if desired.

Topical creams are preferably formulated from a mixture of mineral oil, self-emulsifying beeswax and water in which mixture the active ingredient, dissolved in a small amount of an oil such as almond oil, is admixed. A typical example of such a cream is one which includes about 39 parts water, about 20 parts beeswax, about 40 parts mineral oil and about 1 part almond oil.

Topical ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

Topical lotions may be conveniently prepared by dissolving the active ingredient, in a suitable high molecular weight alcohol such as propylene glycol or polyethylene glycol.

The present invention is more specifically described by the following examples, which are meant to be illustrative only of the process of synthesis and of the novel compounds, both end products and intermediates, obtainable thereby. In these examples, specific compounds identified by Arabic numerals (e.g. compounds 1, 2, 3, . . . etc.) refer to the structures so numbered in the process schematics. Additionally examples are provided which are illustrative of the distinctive biological characteristics of the new compounds, such characteristics serving as a basis for the application of these compounds in the treatment of metabolic bone disease and psoriasis.

Preparation of Compounds

The preparation of 20(22)-dehydrovitamin analogs having the basic structures shown above can be accomplished starting from the diene-protected derivatives of structures III and IV or

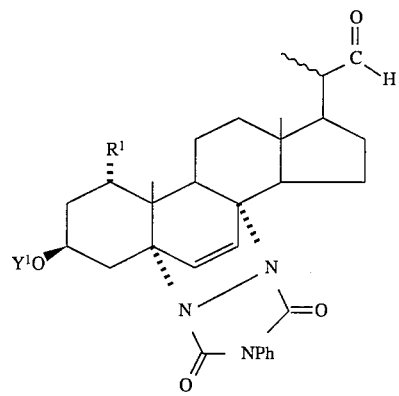

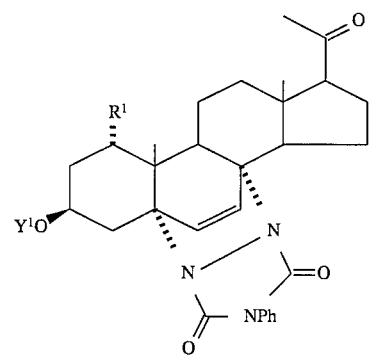

vitamin D compounds of the general structures V through VIII where $Y^1$ and $R^1$ are as defined above.

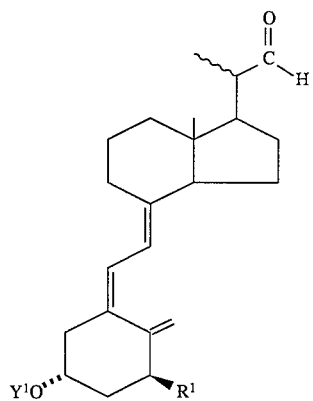

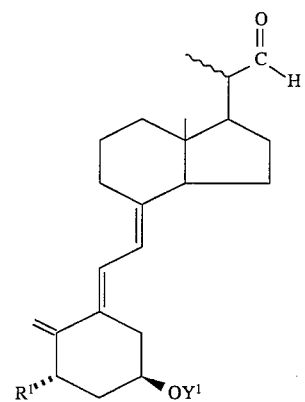

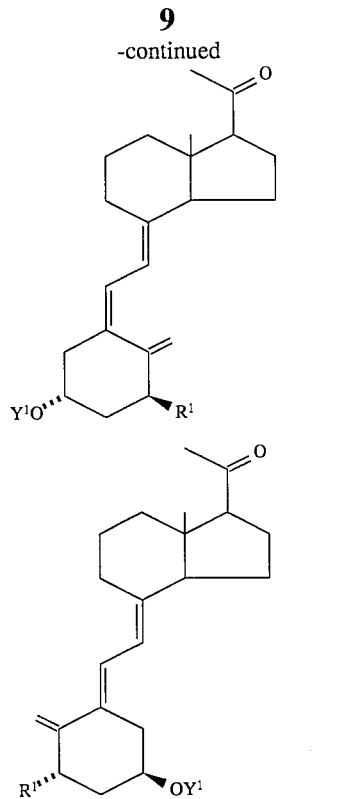

VII

VIII

Reaction of the C-22 aldehydes III, V and VI with the alkylmagnesium halide having the structure RMgX (R as defined above, X=halogen) or alkyllithium reagent having the structure RLi (R as defined above) in the appropriate inert solvent, provides 22-hydroxy compounds of the general formulas IX, X and XI ($Y^2$=H).

The 22-hydroxy intermediates IX, X and XI ($Y^2$=H) having all remaining hydroxy groups protected, can be then directly dehydrated to the 20(22)-dehydro analogs XII, I and II, respectively.

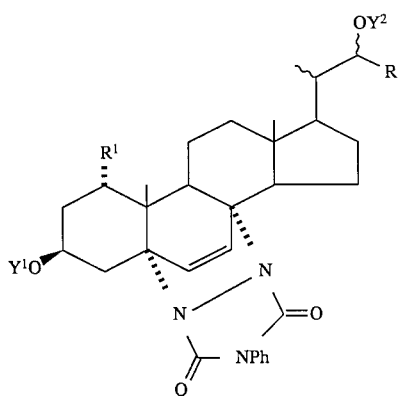

IX

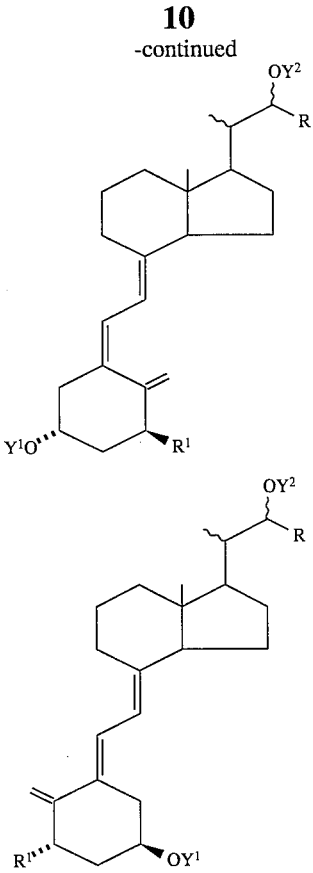

X

XI

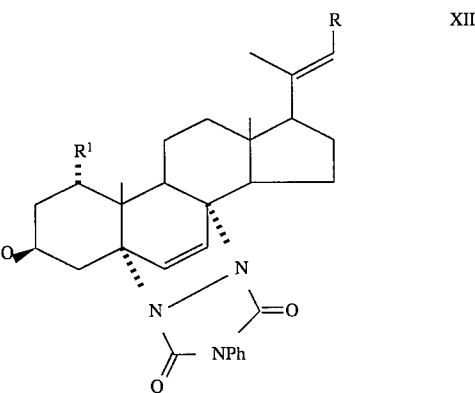

XII

It is well known that dehydration processes of the C-20 alcohols usually give a mixture of isomeric side-chain olefins [(see for example W. R. Ness et al., J. Org. Chem., 41, 3429 (1976)]. It can be therefore advantageous to subject the hydroxy compounds IX, X and XI to the reaction with an alkyl- or arylsulfonylhalide (e.g. methanesulfonyl chloride, p-toluenesulfonyl chloride) in a suitable solvent (e.g. pyridine) and obtain the corresponding 22-O-alkyl- or arylsulfonyl derivatives (the compounds having the structures shown IX, X or XI above, where $Y^2$ is alkyl-$SO_2$— or aryl-$SO_2$—). These compounds are then subjected to the appropriate reaction conditions which promote sulfonate ester 1, 2 elimination process, such as treatment with NaJ, reaction with pyridine, DBU, DBN or another base, reaction on alumina ($Al_2O_3$) column etc. These elimination reactions provide satisfactory yield of (E)-20(22)-compounds I, II and XII. Adduct XII subjected to basic conditions can be then converted to 5,7-diene steroid which in turn, via the well known process consisting of irradiation with UV light and thermal isomerization, gives I.

Alternatively, the 20-ketones IV, VII and VIII can be subjected to Wittig (or Wittig-Horner) reaction with the alkylide-nephophoranes generated from triphenylphosphonium salt having the general formula

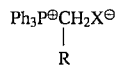

or the phosphinoxy carbanion prepared from the phosphine oxide

(R as defined above, X=halogen) to obtain the corresponding (E)-20(22)-dehydro compounds XII, I and II, respectively. It is well known that Wittig-type reactions with 20-keto steroids afford exclusively 20(22)-unsaturated products with the (E) configuration [see for example S. R. Show et al, J. Org. Chem., 44, 3760 (1979)].

The next step of the process comprises the removal of the hydroxy-protecting groups to produce the free hydroxy compounds represented by vitamin D structures I and II above (where $Y^1$ is hydrogen and $R^1$ can be hydrogen or hydroxyl). If desired, the 5,6-cis compounds I, V, VII and X can be easily converted to the corresponding 5,6-trans counterparts (and vice versa) II, IV, VIII and XI, respectively, by the known iodide-catalyzed isomerization process [see A. Verloop et al., Rec. Trav. Chim. Pays-Bas 78, 1004 (1959)].

EXAMPLE I

Reaction of PTAD-protected diene-aldehyde 1 with Grignard reagent derived from bromocompound A (Scheme I)

A solution of the known 4-bromo-2-methyl-2-triethylsilyloxy) butane A (281 mg, 1 mmol) in anhydrous ether (0.5 mL, containing a catalytic quantity of iodine) was added dropwise to a stirred mixture of magnesium powder (29 mg, 1.2 mmol; ~50 mesh, Aldrich) in anhydrous ether (0.5 mL) under argon at room temperature with occasional warming it up to 35° C. After addition was complete the mixture was stirred for 1 h at room temperature and for 30 min at 40° C. Then it was cooled at 0° C. and a solution of a known PTAD-protected diene (20S)-C-22 aldehyde 1 (123 mg, 0.2 mmol) in anhydrous THF (0.5 mL, cooled to 0° C.) was added dropwise. After the mixture was stirred for 20 min at 0° C. and 1 h at room temperature it was quenched with aqueous solution of $NH_4Cl$ (2 mL) and diluted with benzene (20 mL). The organic layer was separated, washed with brine and diluted $NaHCO_3$, dried ($Na_2SI_4$) and evaporated. Flash chromatography of the residue using 20% ethyl acetate in hexane as an eluent yielded pure (22S)-alcohol 2 (135 mg, 83%) as a foam: $^1$H-NMR ($CDCl_3$, 500 MHz): δ0.084 and 0.106 (3H and 3H, each s, 2×SiMe), 0.578 (6H, q, J=8 Hz, 3×$SiCH_2$), 0.813 (3H, s, 18-$H_3$), 0.885 (9H, s, Si—t—Bu), 0.936 (3H, d, J=7.7 Hz, 21-$H_3$), 0.944 (9H, t, J=8 Hz, 3×$SiCH_2CH_3$), 0.968 (3H, s, 19-$H_3$), 1.222 (6H, br s, 26- and 27- H3), 3.12 (1H, dd, $J_1$= 14.2 Hz, $J_2$=5.1 Hz, 9α-H), 3.65 (1H, m, 22-H), 4.40 (1H, br m, 3α-H), 6.20 and 6.38 (2H, each d, J=8.2 Hz, 6- and 7-H), 7.3–7.5 (5H, br m, Ar—H); MS m/z (rel intensity) 819 ($M^+$, 19), 762 (48), 644 ($M^+$-RDA, 74), 497 (61), 119 (PhNCO, 100).

EXAMPLE 2

Reaction of 22-hydroxy PTAD-protected-diene 2 with p-toluenesulfonyl chloride

To a solution of alcohol 2 (75 mg, 0.093 mmol) in dry pyridine (200 µl) was added fleshly recrystallized p-toluenesulfonyl chloride (49 mg, 0.26 mmol) and the reaction was allowed to proceed for 64 h at 4° C. The reaction mixture was poured into ice/saturated $NaHCO_3$ with stirring. After 40 min. of stirring the aqueous suspension was extracted with 1:1 (v/v) benzene/ether (3×10 mL). The combined extracts were washed with saturated $NaHCO_3$, water, saturated $CuSO_4$, again water, dried ($Na_2SO_4$) and evaporated. The oily yellowish residue (quantitative yield) was pure enough to be used for the subsequent synthetic step. Analytical sample of the tosylate 3 was obtained after HPLC purification (Zorbax-Silica column 6.2 mm×25 cm) using 10% ethyl acetate in hexane ($R_v$ 16 mL): $^1$H-NMR ($CDCl_3$, 500 MHz): δ0.089 and 0.108 (3H and 3H, each s, 2×SiMe), 0.537 (6H, q, J=7.9 Hz, 3×$SiCH_2$), 0.723 (3H, s, 18-$H_3$), 0.887 (9H, s, Si—t—Bu), 0.921 (9H, t, J=7.9 Hz, 3×$SiCH_2CH_3$), ~0.94 (3H, d, J=7 Hz, 21-$H_3$), 0.943 (3H, s, 19-$H_3$), 1.123 and 1.157 (3H and 3H, each s, 26- and 27-$H_3$), 2.43 (3H, s, Ar—Me), 3.13 (1H, dd, $J_1$ =14.2 Hz, $J_2$ =5.0 Hz, 9α-H), 4.39 (1H, br m, 3α-H), 4.49 (1H, t, J=7.0 Hz, 22-H), 6.18 and 6.30 (2H, each d, J=8.3 Hz, 6- and 7- H), 7.3–7.5 (7H, br m, Ar—H), 7.79 (2H, d, J=8.2 Hz, Ar—H).

EXAMPLE 3

Reaction of 22-tosyloxy PTAD-protected diene 3 with sodium iodide

To a stirred solution of tosylate 3 (4.9 mg, 5 µmol) in 1:1 (v/v) acetone/2-butanone (200 µL) was added calcium carbonate (1 mg, 10 µmol) followed by sodium iodide (3.7 mg, 25 µmol). The resultant mixture was stirred and heated for 80 h at 55° C. under argon, by which time no starting material remained. The reaction mixture was poured into water (10 mL) and extracted with ethyl acetate (2×10 mL). The combined organic layers were washed with 1% $Na_2SO_3$ and water, dried ($Na_2SO_4$) and evaporated. The residue was separated by preparative HPLC (6.2 mm×25 cm Zorbax-Silica column) using 3% ethyl acetate in hexane as an eluent. Pure (E)-20(22)-dehydro compound 4 (2.2 mg, 55%; collected at 52 mL) was obtained as a foam: $^1$H-NMR ($CDCl_3$, 500 MHz): δ0.087 and 0.109 (3H and 3H, each s, 2×SiMe), 0.571 (6H, q, J=8 Hz, 3×$SiCH_2$), 0.658 (3H, s, 18-$H_3$), 0.888 (9H, s, Si—t—Bu), 0.950 (9H, s, 26- and 27-$H_3$), 1.639 (3H, s, 21-$H_3$), 3.13 (1H, dd, $J_1$ =14.1 Hz, $J_2$=5.1 Hz, 9α-H), 4.40 (1H, br m, 3α-H), 5.23 (1H, t, J=7.0 Hz, 22-H), 6.19 and 6.36 (2H, each d, J=8.3 Hz, 6- and 7-H), 7.3–7.5 (5H, br m, Ar—H): MS m/z (rel intensity) 801 ($M^+$, <1) 626 ($M^+$-RDA, 100), 479 (77), 119 (PhNCO, 58).

Compound 4 is a direct precursor of the (E)-20(22)-dehydrovitamin $D_3$.

EXAMPLE 4

Elimination of p-toluenesulfonate ester 3 in pyridine

A solution of tosylate 3 (1 mg, 1 µmol) in a dry pyridine (200 µl ) was heated under argon for 48 h at 70° C. Solvent was evaporated, the residue taken up in ethyl acetate and the solution was washed with saturated $CuSO_4$, water and saturated $NaHCO_3$, dried ($Na_2SO_4$) and evaporated. HPLC separation of the residue (6.2 mm×25 cm Zorbax-Silica column) using 3% ethyl acetate in hexane yielded the olefin 4 (0.29 mg, 35%; collected at 52 mL).

EXAMPLE 5

Reaction of vitamin D C-22 aldehyde 5 with Grignard reagent derived from bromocompound A A solution of 4-bromo-2-methyl-2-triethylsilyloxy) butane A (94 mg, 0.33 mmol) in anhydrous ether (0.3 mL) was added dropwise to a stirred mixture of magnesium powder (9.7 mg, 0.4 mmol; ~50 mesh, Aldrich) in anhydrous ether (0.2 mL) under argon at room temperature with occasional warming it up to 35° C. After addition was complete the mixture was stirred for 15 min. at room temperature and 30 min. at 40° C. Then it was cooled to 0° C. and a solution of a known (20S)-C-22 vitamin aldehyde 5 [(32 mg, 0.056 mmol; see A. Kutner et al., J. Org. Chem. 53, 3450 (1988)] in anhydrous ether (0.3 mL, cooled to 0° C.) was added dropwise. After the mixture was stirred for 20 min at 0° C. and 75 min. at room temperature it was quenched with aqueous solution of $NH_4Cl$ (2 mL) and diluted with 4:1 (v/v) benzene/ether (20 mL). The organic layer was separated, washed with brine and diluted $NaHCO_3$, dried ($Na_2SO_4$) and evaporated. TLC and HPLC control indicated formation of only one (22S) of the two possible isomers. Pure (22S)-hydroxyvitamin D derivative 6 was obtained as a colorless oil (31 mg, 75%) by preparative HPLC (Zorbax-Silica column 6.2 mm× 25 cm) using 3.5% ethyl acetate in hexane as an eluent; peak at 30 mL was collected. UV (EtOH).$\lambda_{max}$ 264 nm, $\lambda_{min}$ 225 nm, $A_{264}/A_{265}$=1.6; $^1$H-NMR (CDCl$_3$, 500 MHz): δ0.062 (12H, br s, 4×SiMe), 0.546 (3H, s, 18-H$_3$), 0.583 (6H, q, J=8 Hz, 3×SiCH$_2$), 0.887 (18H, s, 2×Si—t—Bu), 0.920 (3H, d, J=6.4 Hz, 21-H$_3$), 0.947 (9H, t, J=8 Hz, 3×SiCH$_2$CH$_3$), 1.221 and 1.225 (3H and 3H, each s, 26- and 27-H$_3$), 2.83 (1H, br d, J=12.5 Hz, 9β-H), 3.63 (1H, m, 22-H), 4.19 (1H, m, 3α-H), 4.37 (1H, m, 1β-H), 4.87 and 5.18 (1H and 1H, each s, 19-H$_2$), 6.02 (1H, d, J=11.2 Hz, 7-H), 6.24 (1H, d, J=11.2 Hz, 6-H); MS m/z (rel intensity) 774 (M$^+$, 15), 642 (43), 75 (100); exact mass calcd for $C_{45}H_{86}O_4Si_3$ 774.5834, found 774.5850.

EXAMPLE 6

Reaction of 22-hydroxyvitamin D compound 6 with p-toluenesulfonyl chloride

To a solution of alcohol 6 (28 mg, 0.036 mmol) in dry pyridine (100 μl) was added freshly recrystallized p-toluenesulfonyl chloride (20 mg, 0.10 mmol) and the reaction was allowed to proceed for 64 h at 4° C. The reaction mixture was poured into ice/saturated $NaHCO_3$ with stirring. After 40 min. of stirring the aqueous suspension was extracted with 4:1 (v/v) benzene/ether (3×10 mL). The combined extracts were washed with saturated $NaHCO_3$, water, saturated $CuSO_4$, again water, dried ($Na_2SO_4$) and evaporated. The oily yellowish residue was purified by preparative HPLC (Zorbax-Silica column 6.2 mm×25 cm) using 2% ethyl acetate in hexane as an eluent. Pure tosylate 7 was obtained as a colorless oil: UV (hexane) $\lambda_{max}$ 264 and 223 nm, $\lambda_{min}$ 238 nm; $^1$H-NMR (CDCl$_3$, 500 MHz): δ0.059 and 0.067 (6H and 6H, each s, 2×SiMe$_2$), 0.479 (3H, s, 18-H$_3$), 0.528 (6H, q, J=8 Hz, 3×SiCH$_2$), 0.877 (18H, s, 2× Si—t—Bu), 0.915 (9H, t, J=8 Hz, 3×SiCH$_2$ CH$_3$), 0.929 (3H, d, J=6.0 Hz, 21-H$_3$), 1.103 and 1.141 (3H and 3H, each s, 26- and 27-H$_3$), 2.43 (3H, s, Ar—Me), 2.80 (1H, br d, J=12.3 Hz, 9β-H), 4.19 (1H, m, 3α-H), 4.38 (1H, m, 1β-H), 4.58 (1H, t, J=7.1 Hz, 22-H), 4.86 and 5.19 (1H and 1H, each s, 19-H$_2$), 5.99 (1H, d, J=11.2 Hz, 7-H), 6.22 (1H, d, J=11.2 Hz, 6-H), 7.32 (2H, d, J=8 Hz, Ar—H), 7.80 (2H, d, J=8 Hz, Ar—H); MS m/z (rel intensity) 928 (M$^+$, 1), 796 (2), 756 (3), 664 (3), 624 (47), 492 (27), 173 (100); exact mass calcd for $C_{52}H_{92}O_6Si_3S$ 928.5922, found 928.5894.

EXAMPLE 7

Reaction of vitamin D 22-p-toluenesulfonate 7 with sodium iodide

To a stirred solution of tosylate 7 (4.6 mg, 5 μmol) in 1:1 (v/v) acetone/2-butanone (200 μL) was added calcium carbonate (1 mg, 10 μmol) followed by sodium iodide (3.7 mg, 25 μmol). The resultant mixture was stirred and heated for 100 h at 45° C. in the dark under argon, by which time no stating material remained. The reaction mixture was poured into water (10 mL) and extracted with ethyl acetate (2×10 mL). The combined organic layers were washed with 1% $Na_2SO_3$ and water, dried ($Na_2SO_4$) and evaporated. The work up of the reaction mixture and following chromatographic separations were done using subdued light in the laboratory. The mixture of products was separated by preparative HPLC (6.2 mm×25 cm Zorbax-Silica column) using 0.1% ethyl acetate in hexane as an eluent. The main product 8 (peak at R$_v$ 34 mL) was isolated and repurified by HPLC in the same solvent system (recycling mode) to give an analytically pure material (1.2 mg, 32%): UV (hexane) $\lambda_{max}$ 265.0 nm, $\lambda_{min}$ 228.5 nm ($A_{265}/A_{228}$=1.7); $^1$H-NMR (CDCl$_3$, 500 MHz): δ0.063 and 0.072 (6H and 6H, each s, 2×SiMe$_2$), 0.403 (3H, s, 18-H$_3$), 0.567 (6H, q, J=8 Hz, 3×SiCH$_2$), 0.884 (18H, s, 2×Si—t—Bu), 0.946 (9H, t, J=8 Hz, 3×SiCH$_2$CH$_3$), 1.264 (6H, br s, 26- and 27-H$_3$), 1.630 (3H, s, 21-H$_3$), 2.84 (1 H, br d, J=12.8 Hz, 9β-H), 4.19 (1H, m, 3α-H), 4.38 (1H, m, 1β-H), 4.87 (1H, s, one of 19-H$_2$), 5.19 (2H, m, one of 19-H$_2$ and 22-H), 6.02 (1H, d, J=11.2 Hz, 7-H), 6.24 (1H, d, J=11.2 Hz, 6-H); MS m/z (rel intensity) 756 (M$^+$, 12), 624 (31), 248 (47), 117 (100); exact mass calcd for $C_{45}H_{84}O_3Si_3$ 756.5728, found 756.5707.

EXAMPLE 8

Deprotection of hydroxyl groups in (E)-20(22)-dehydro compound 8

To a solution of protected triol 8 (0.93 mg, 1.22 μmol) in anhydrous benzene (40 μl) was added AG 50W-X$_4$ ion exchange resin (15 mg, prewashed with methanol) as a slurry in anhydrous methanol (200 μL). The mixture was vigorously stirred at room temperature for 13 h under argon, and it was diluted with 1:1 (v/v) ether/ethyl acetate (1 mL). The solution was decanted and transferred to separatory funnel and the resin was washed with 1:1 ether/ethyl acetate (2×2 mL). The combined organic phase was washed with 5 nL portions of brine, 1% $Na_2S_2O_3$, saturated $NaHCO_3$, and brine again, dried ($Na_2SO_4$) and evaporated. Purification of product by HPLC (6.2 mm×25 cm Zorbax-Silica column) using 1:1 (v/v) hexane/ethyl acetate as an eluent provided crystalline triol 9 (337 μg, 66%; eluted at R$_v$ 59 mL): UV (EtOH) $\lambda_{max}$ 265.0 nm, $\lambda_{min}$ 228.5 nm ($A_{265}/A_{228}$=1.8); $^1$H=NMR (CDCl$_3$, 500 MHz): δ0.424 (3H, s, 18-H$_3$), 1.231 (6H, br s, 26- and 27-H$_3$), 1.651 (3H, s, 21-H$_3$), 2.84 (1H, br d, J=12.2 Hz, 9β-H), 4.23 (1H, m, 3α-H), 4.44 (1H, m, 1β-H), 5.00 (1H, s, one of 19-H$_2$), 5.23 (1H, t, J=7.1 Hz, 22-H), 5.33 (1H, s, one of 19-H$_2$), 6.03 (1H, d, J=11.3 Hz, 7-H), 6.38 (1H, d, J=11.3 Hz, 6-H); MS m/z (rel intensity) 414 (M$^+$, 8) 396 (M$^+$-H$_2$O, 15), 378 (M$^+$-2H$_2$O, 10), 152 (37), 134 (100); exact mass calcd for $C_{27}H_{42}O_3$ 414.3134, found 414.3138.

Scheme I
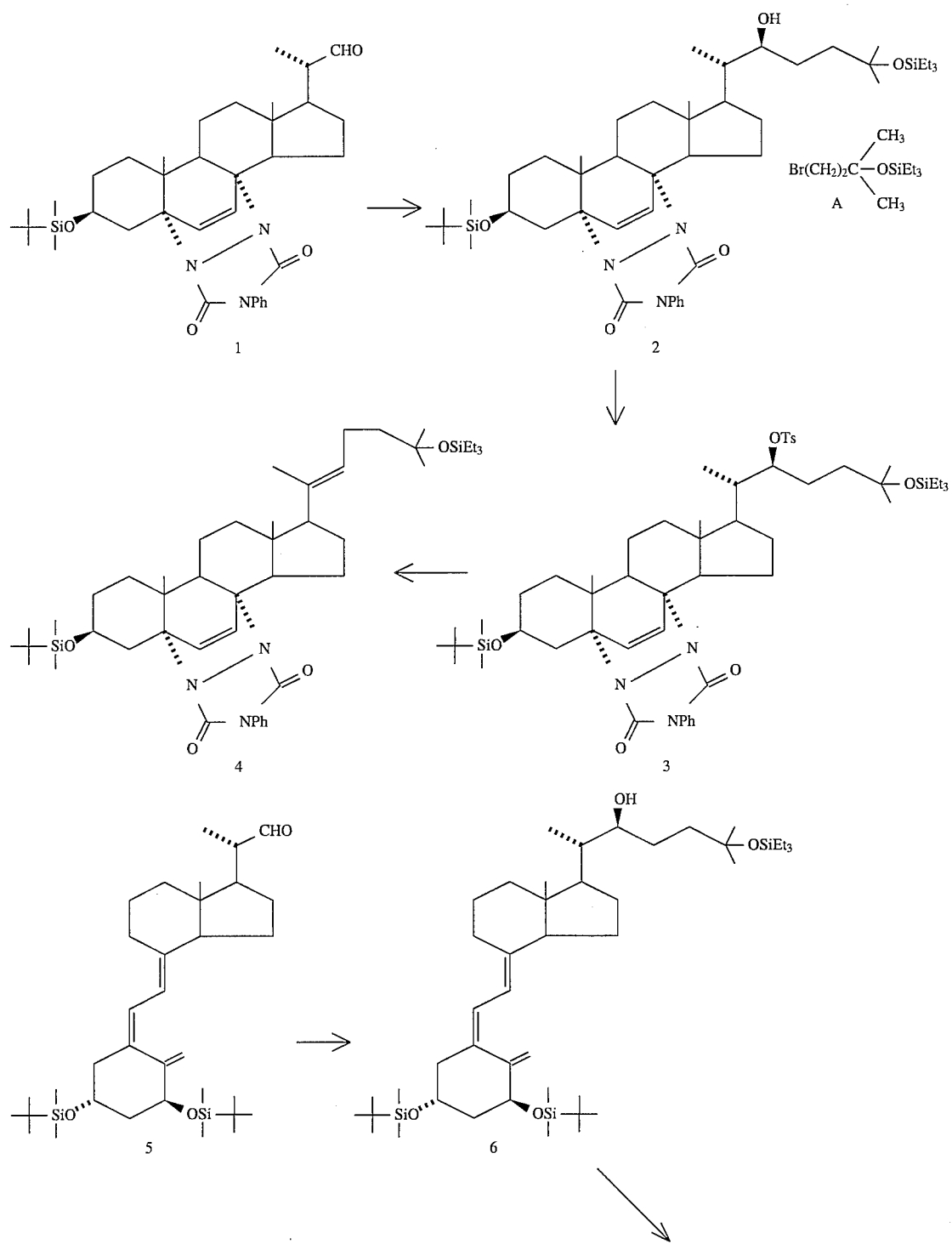

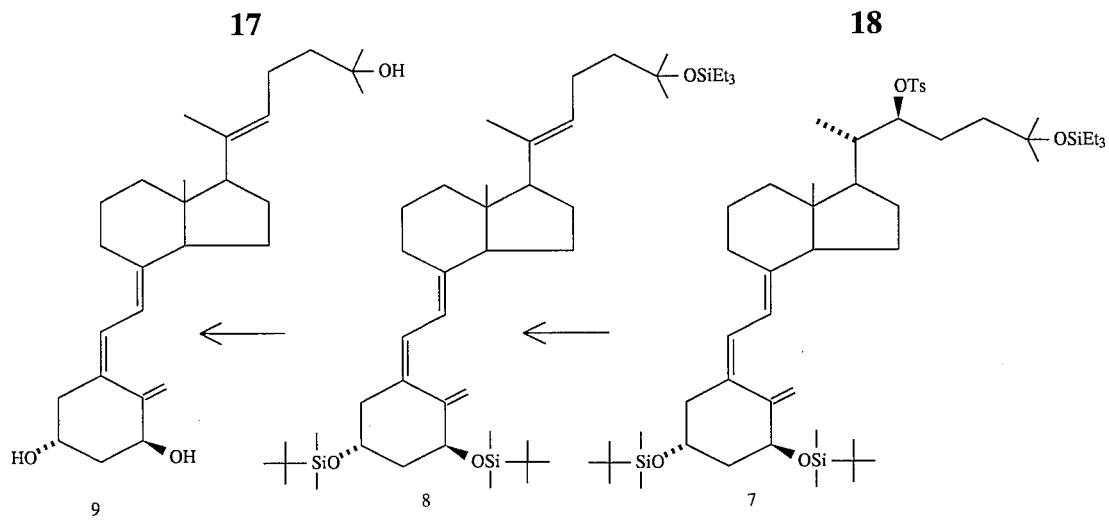

Biological Activity

Rats were maintained on a normal calcium and normal phosphorus diet for one week (0.47% Ca, 0.3% P), then switched to a -Ca diet for the duration of the experiment (0.02% Ca). Vitamin D compounds were suspended in mixtures of ethanol and propylene glycol (5%:95%) and were administered daily for 6 days intraperitoneally.

After 6 days the rats were killed and the duodena were used for determination of intestinal calcium transport by the everted intestinal sac technique (Martin & DeLuca, 1967) and serum calcium (bone calcium mobilization). The tests were made against the 1,25-dihydroxyvitamin $D_3$ standard and are reported in Table 1.

TABLE 1

INTESTINAL CALCIUM TRANSPORT AND BONE CALCIUM MOBILIZING ACTIVITIES OF (E)-20(22)-DEHYDRO-1α,25-DIHYDROXYVITAMIN $D_3$

| Compound | Amount (μgs/d/ 6 days) | S/M (ave. s.e.m.) | Serum Ca (ave. s.e.m.) (mg %) |
|---|---|---|---|
| D-Deficient | 0 | 3.98 +/− 0.19 | 4.14 +/− 0.07 |
| 1α,25-(OH)$_2$D$_3$ | 0.1 μg/d | 11.2 +/− 1.2 | 5.9 +/− 0.27 |
| (E)-20(22)-dehydro-1α,25-(OH)$_2$D$_3$ | 1 μg/d | 12.4 +/− 0.73 | 5.2 +/− 0.23 |

The results show that the (E)-20(22)-dehydro-1,25-dihydroxyvitamin $D_3$ compound is less active than 1,25-dihydroxyvitamin $D_3$ in mobilization of calcium from bone since the serum calcium levels of the compound are less than that found for 1α,25-dihydroxyvitamin $D_3$ even though the dosage is 10 times greater. However, the (E)-20(22)-dehydro-1,25-dihydroxyvitamin $D_3$ compound has highly significant intestinal calcium transport activity. These compounds therefore, by showing preferential activity on intestinal calcium transport and reduced calcium mobilizing activity in bone suggest that they are preferred agents for the treatment of a disease where bone loss is a major issue, such as osteoporosis, osteomalacia and renal osteodystrophy.

Measurement of Differentiation in HL-60 Cells

The measurement of differentiation in HL-60 cells (human leukemia cells) was carried out according to the general procedures described by DeLuca et al., U.S. Pat. No. 4,717,721. As shown in Table 2, degree of differentiation is assessed by a standard assay, namely, NBT reduction, and results are expressed as the percent of differentiated cells produced in response to treatment with various concentrations of vitamin D compounds.

TABLE 2

Differentiation Activity in HL-60 Cells in Culture

| Compound | Concentration (molar) | % Cells Showing Differentiation NBT Reduction |
|---|---|---|
| 1,25-(OH)$_2$D$_3$ | 1 × 10$^{-7}$ | 90 ± 2 |
| | 5 × 10$^{-8}$ | 69 ± 3 |
| | 1 × 10$^{-8}$ | 58 ± 3 |
| | 1 × 10$^{-9}$ | 36 ± 2 |
| Δ$^{20(22)}$-1,25(OH)$_2$D$_3$ | 1 × 10$^{-7}$ | 85 ± 3 |
| | 5 × 10$^{-8}$ | 67 ± 3 |
| | 1 × 10$^{-8}$ | 34 ± 2 |
| | 1 × 10$^{-9}$ | 12 ± 2 |

The results of this assay is shown in Table 2. It is evident that the novel analogs are about equally as active as 1,25-(OH)$_2$D$_3$ itself in causing differentiation of HL-60 cells in culture.

For treatment purposes, the novel compounds of this invention may be formulated for pharmaceutical applications as a solution in innocuous solvents, or as an emulsion, suspension or dispersion in suitable solvents or carriers, or as pills, tablets or capsules together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds may be administered orally, topically, parenterally or transdermally. The compounds are advantageously administered by injection or by intravenous infusion of suitable sterile solutions, or in the form of liquid or solid doses via the alimentary canal, or in the form of creams, ointments, patches, or similar vehicles suitable for transdermal applications. Doses of from 0.5 μg to 50 μg per day of the compounds are appropriate for treatment purposes, such doses being adjusted according to the disease to be treated, its severity and the response of the subject, as is well understood in the art. Since the new compounds exhibit specificity of action, each may be suitably administered alone, in situations where only calcium transport stimulation is desired, or together with graded doses of another active vitamin D compound—e.g. 1α-hydroxyvitamin $D_2$ or $D_3$, or 1α,25-dihydroxyvitamin $D_3$—in situations where some degree of bone mineral mobilization (together with calcium transport stimulation) is found to be advantageous.

Various modes of carrying out the invention are contemplated as being within the scope of the following claims particularly pointing out and distinctly claiming the subject matter regarded as the invention.

We claim:

1. A compound having the formula:

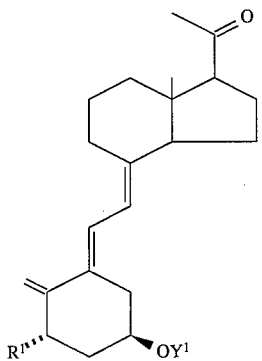

where $Y^1$ is hydrogen or a hydroxy-protecting group, and $R^1$ represents hydrogen, hydroxy or protected hydroxy.

* * * * *